(12) United States Patent
Gross

(10) Patent No.: US 8,135,478 B2
(45) Date of Patent: Mar. 13, 2012

(54) PELTIER UNIDIRECTIONAL AND SELECTIVE NERVE STIMULATION

(75) Inventor: Yossi Gross, Moshav Mazor (IL)

(73) Assignee: Rainbow Medical Ltd, Herzliya (IL)

( * ) Notice: Subject to any disclaimer, the term of this patent is extended or adjusted under 35 U.S.C. 154(b) by 612 days.

(21) Appl. No.: 12/352,644

(22) Filed: Jan. 13, 2009

(65) Prior Publication Data

US 2009/0187223 A1  Jul. 23, 2009

Related U.S. Application Data

(63) Continuation-in-part of application No. 11/487,012, filed on Jul. 13, 2006, now Pat. No. 7,761,168, and a continuation-in-part of application No. PCT/IL2007/000854, filed on Jul. 8, 2007.

(51) Int. Cl.
*A61N 1/18* (2006.01)

(52) U.S. Cl. .............. 607/118; 607/2; 607/63; 607/115

(58) Field of Classification Search .............. 607/2–3, 607/45–46, 63, 115–118; 600/377–378
See application file for complete search history.

(56) References Cited

U.S. PATENT DOCUMENTS

| | | | |
|---|---|---|---|
| 4,483,341 A | 11/1984 | Witteles | |
| 5,228,923 A | 7/1993 | Hed | |
| 5,824,027 A | 10/1998 | Hoffer et al. | |
| 5,876,422 A | 3/1999 | Van Groeningen | |
| 6,178,349 B1 | 1/2001 | Kieval | |
| 6,629,990 B2 | 10/2003 | Putz et al. | |
| 6,736,837 B2 | 5/2004 | Fox | |
| 6,746,474 B2 | 6/2004 | Saadat | |
| 6,839,594 B2 | 1/2005 | Cohen et al. | |
| 6,907,295 B2 | 6/2005 | Gross et al. | |
| 2003/0028229 A1 | 2/2003 | Rothman | |
| 2004/0122475 A1* | 6/2004 | Myrick et al. | 607/2 |
| 2004/0167581 A1 | 8/2004 | Mower | |
| 2004/0172085 A1 | 9/2004 | Knudson et al. | |
| 2004/0210286 A1 | 10/2004 | Saadat | |
| 2005/0131485 A1 | 6/2005 | Knudson et al. | |
| 2005/0234523 A1 | 10/2005 | Levin et al. | |
| 2006/0100668 A1 | 5/2006 | Ben-David et al. | |
| 2008/0015667 A1 | 1/2008 | Gross | |

FOREIGN PATENT DOCUMENTS

| | | |
|---|---|---|
| WO | WO 03/101354 | 12/2003 |
| WO | WO 2004/062481 | 1/2004 |
| WO | WO 2004/032720 | 4/2004 |
| WO | WO 2008/007360 | 1/2008 |

* cited by examiner

*Primary Examiner* — Carl H Layno
*Assistant Examiner* — Paula J Stice
(74) *Attorney, Agent, or Firm* — Stein McEwen, LLP

(57) ABSTRACT

Apparatus is provided including an assembly (22) and a control unit (36). The assembly (22) includes a housing (34) configured to be applied to a nerve (20) of a subject, and at least one cathode (30) and at least one Peltier cooler (32), which are fixed to the housing (34). The control unit (36) is configured to drive the cathode (30) to apply an activating current to the nerve (20) that generates action potentials traveling in first and second directions (38 and 40) in the nerve (20), and the Peltier cooler (32) to cool the nerve (20) sufficiently to block propagation of at least a portion of the cathode-generated action potentials traveling in the second direction (40). Other embodiments are also described.

16 Claims, 5 Drawing Sheets

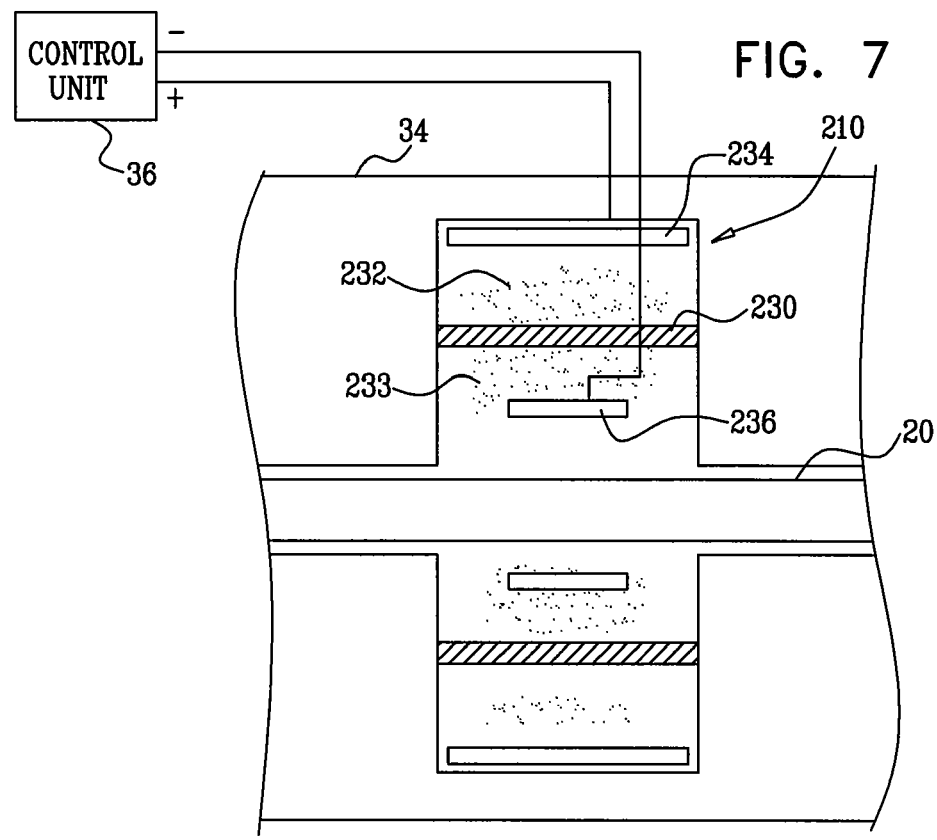
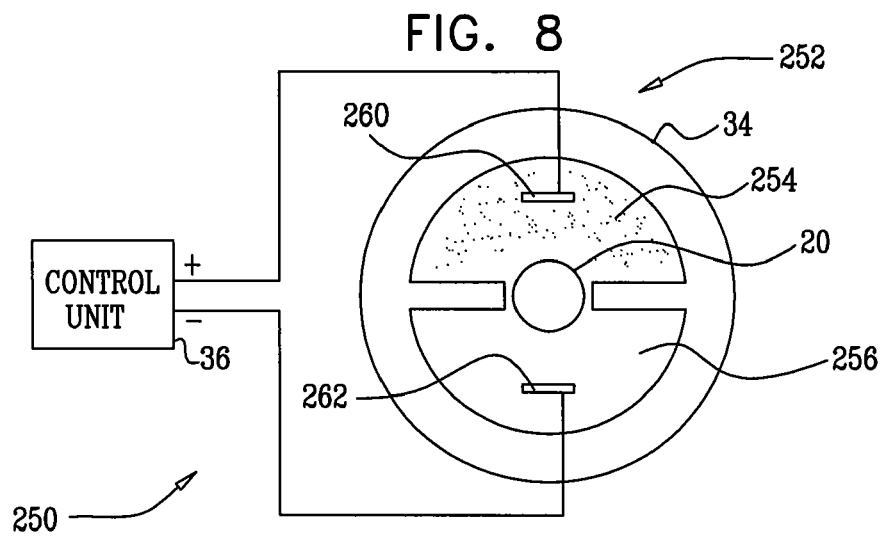

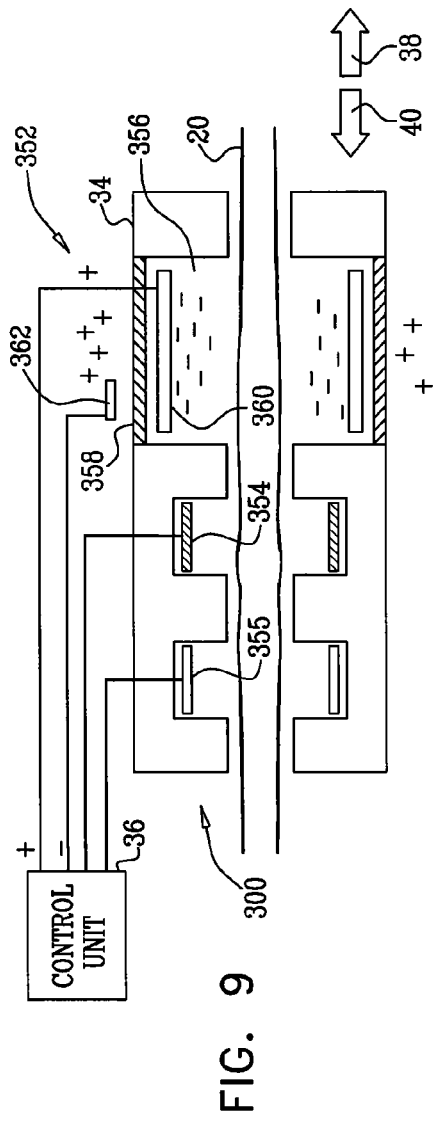
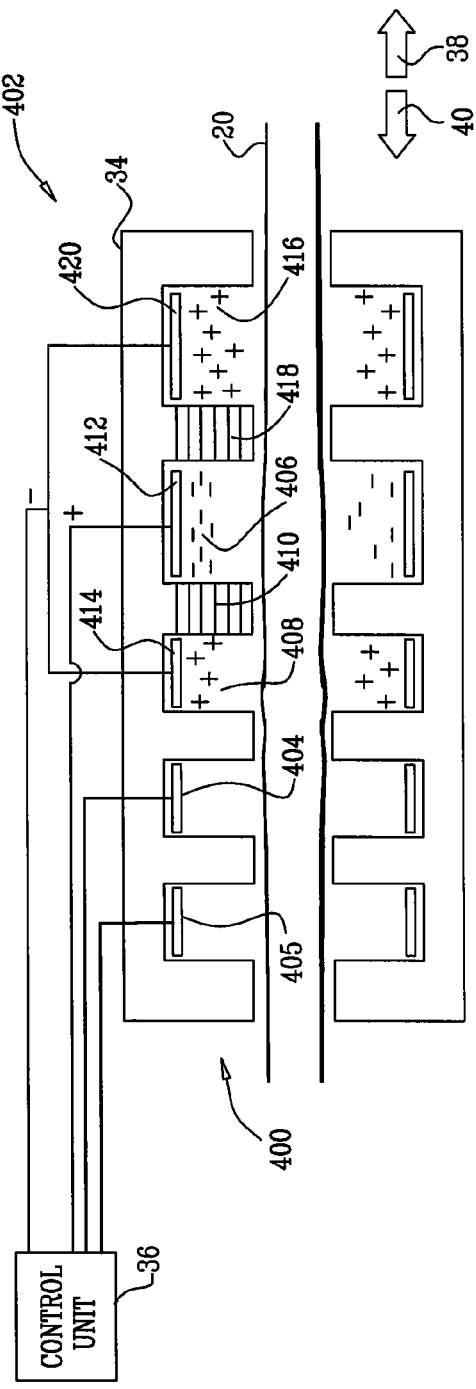

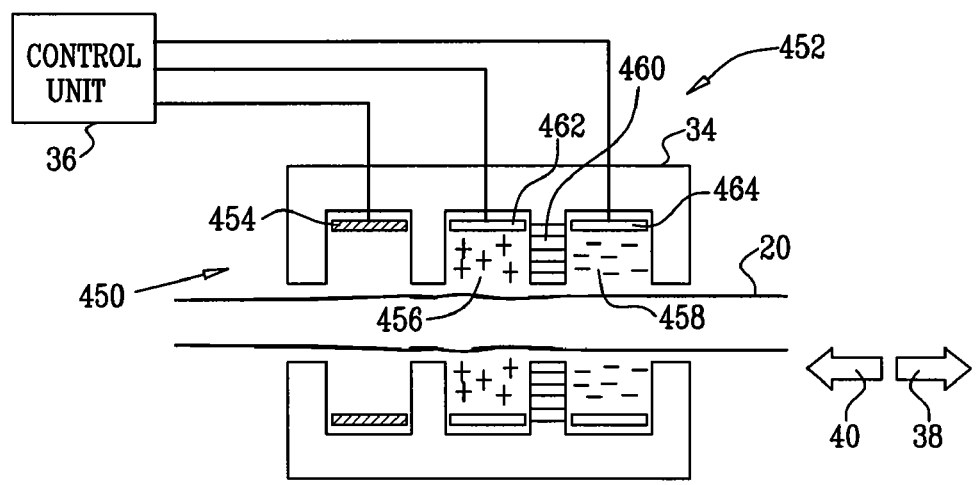
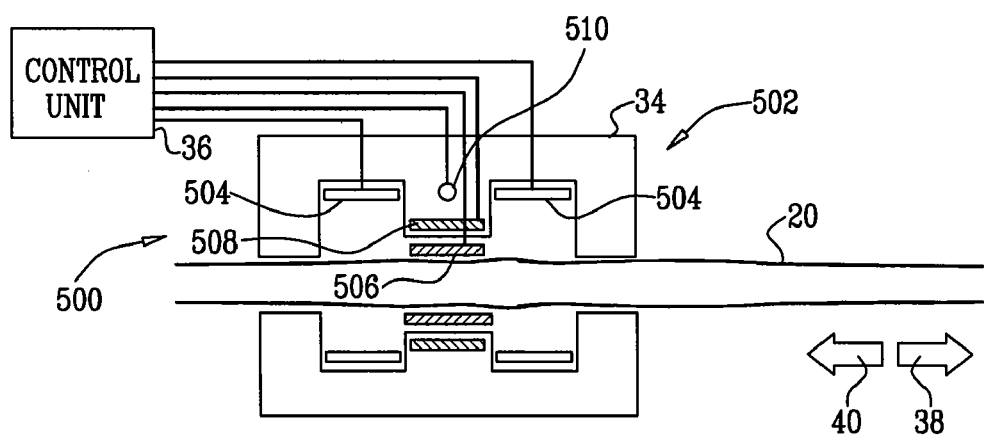

PELTIER UNIDIRECTIONAL AND SELECTIVE NERVE STIMULATION

CROSS-REFERENCES TO RELATED APPLICATIONS

This application is a continuation-in-part of (a) PCT Application PCT/IL2007/000854 to Gross, filed Jul. 8, 2007, entitled, "Peltier unidirectional and selective nerve stimulation," and (b) U.S. patent application Ser. No. 11/487,012 to Gross, filed Jul. 13, 2006, entitled, "Peltier unidirectional and selective nerve stimulation," both of which applications are incorporated herein by reference.

FIELD OF THE INVENTION

The present invention relates generally to implantable medical devices, and specifically to apparatus and methods for nerve stimulation.

BACKGROUND OF THE INVENTION

The Peltier effect is the creation of a heat difference by an electric voltage. The effect occurs when a current is passed through two dissimilar metals or semiconductors that are connected to one another at two junctions (Peltier junctions). The current drives a transfer of heat from one junction to the other, such that one of the junctions is cooled and the other is heated. Peltier coolers, also called thermo-electric coolers, are solid-state devices that utilize the Peltier effect for heating and/or cooling.

The following patents and patent applications may be of interest:
U.S. Pat. No. 4,483,341 to Witteles
U.S. Pat. No. 5,228,923 to Hed
U.S. Pat. No. 5,876,422 to van Groeningen
U.S. Pat. No. 6,178,349 to Kieval
U.S. Pat. No. 6,629,990 to Putz et al.
U.S. Pat. No. 6,736,837 to Fox
U.S. Pat. No. 6,746,474 to Saadat
U.S. Pat. No. 6,839,594 to Cohen et al.
PCT Publication WO 03/101354 to Saadat
PCT Publication WO 04/032720 to Osorio et al.
PCT Publication WO 04/062481 to Mower
U.S. Patent Application Publication 2003/0028229 to Rothman
U.S. Patent Application Publication 2004/0167581 to Mower
U.S. Patent Application Publication 2004/0210286 to Saadat

SUMMARY OF THE INVENTION

In some embodiments of the present invention, an assembly for stimulating a nerve comprises at least one cathode and at least one Peltier cooler, which are fixed to a housing. A control unit drives the cathode to apply a current to the nerve that generates action potentials traveling in first and second directions in the nerve, and drives the Peltier cooler to cool the nerve, thereby blocking propagation of the cathode-generated action potentials traveling in the second direction. As a result, the assembly generates unidirectional action potentials in the nerve traveling in the first direction. For some applications, the assembly comprises at least one anode, while for other applications, at least one anode remote from the assembly is provided, e.g., the control unit serves as the anode.

Techniques known in the art for achieving unidirectional blocking by the application of an anodal current sometimes generate undesired action potentials, such as pain signals traveling towards the brain. In contrast, the Peltier cooling techniques of these embodiments of the present invention do not generate any such action potentials.

In some embodiments of the present invention, an assembly for stimulating a nerve comprises at least one cathode, at least one anode, and at least one Peltier cooler, which are fixed to a housing. A control unit drives the cathode to apply a current to the nerve that generates action potentials traveling in first and second directions in the nerve, and the anode to apply an inhibiting current to the nerve that partially blocks propagation of the cathode-generated action potentials traveling in the second direction. The control unit also drives the Peltier cooler to block propagation of the cathode-generated action potentials traveling in the second direction. As a result, the assembly generates unidirectional action potentials in the nerve traveling in the first direction. The anodal blocking in combination with the Peltier blocking provides more effective blocking than anodal blocking alone is typically able to achieve.

In some embodiments of the present invention, an assembly for stimulating a nerve comprises at least one cathode and at least one Peltier cooler, which are fixed to a housing. A control unit drives the cathode to apply a current to the nerve that generates action potentials in fibers of the nerve up to a first depth from the surface of the nerve, and the Peltier cooler to cool fibers of the nerve up to a second depth less than the first depth, thereby blocking propagation of the cathode-generated action potentials traveling in the fibers of the nerve up to the second depth. As a result, the assembly generates action potentials only in fibers of the nerve located between the first and second depths. For some applications, the first depth equals substantially the radius of the nerve, such that the cathode generates action potentials in all fibers of the nerve, a portion of which are blocked by the Peltier cooler.

In some embodiments of the present invention, an assembly for stimulating a nerve comprises at least one cathode, at least one anode, and at least one Peltier cooler, which are fixed to a housing. A control unit drives the assembly to selectively recruit nerve fibers of intermediate diameter, by: (a) driving the cathode to generate action potentials in fibers essentially of all diameters, (b) driving the anode to inhibit the cathode-generated action potentials in larger-diameter fibers, and (c) driving the Peltier cooler to inhibit the cathode-generated action potentials in smaller-diameter fibers. Alternatively, the assembly does not include the anode that inhibits the action potentials in the larger-diameter fibers, and the assembly therefore is suitable for use for recruiting larger-diameter fibers. In either case, for some applications, the assembly comprises at least one second anode and/or at least one second Peltier cooler, which the control unit drives to block cathode-generated action potentials traveling in an undesired direction in the nerve, as described hereinabove. It is noted that while electrical inhibition typically affects larger fibers first, inhibition by cooling typically affects smaller fibers first.

In some embodiments of the present invention, an assembly for stimulating a nerve comprises at least two Peltier coolers and at least one cathode positioned between the coolers, which are fixed to a housing. A control unit drives the cathode to generate action potentials in the nerve traveling in both directions. The control unit drives a first one of the coolers to block substantially all of the cathode-generated action potentials traveling towards the first cooler, and a second one of the coolers to block cathode-generated action potentials traveling towards the second cooler in fibers of the nerve up to a certain depth from the surface of the nerve. As a result, the assembly generates selective-fiber-depth unidirectional action potentials.

Alternatively or additionally, the control unit drives the second one of the coolers to block cathode-generated action potentials traveling towards the second cooler in smaller fibers of the nerve. As a result, the assembly generates selective-fiber-diameter unidirectional action potentials.

In some embodiments of the present invention, an assembly for stimulating a nerve comprises a housing, having fixed thereto one or more anodes, e.g., at least two anodes, and at least one cathode positioned adjacent to or between the anodes. The assembly further comprises a heating element positioned near the cathode. For some applications, the cathode serves as the heating element. A control unit drives the cathode and anodes to apply a current to the nerve, and the heating element to heat the nerve slightly, without causing damage thereto. The heat causes smaller-diameter fibers within the nerve to be more sensitive to the cathodic stimulation than are larger-diameter fibers. As a result, the assembly recruits smaller-diameter fibers with lower applied current than would occur without the heating. Typically, the assembly selectively recruits nerve fibers beginning with smaller-diameter fibers, and progressively recruits larger-diameter fibers as the desired stimulation level increases, or, alternatively, recruits smaller- and larger-diameter fibers substantially equally as the desired stimulation level increases, rather than first recruiting larger-diameter fibers as generally occurs when using conventional nerve stimulation techniques. Further alternatively, the assembly in any case recruits larger-diameter fibers earlier than smaller-diameter fibers, but the difference is less extreme than would be the case in the absence of the slight heating.

In some embodiments of the present invention, an assembly for blocking action potential propagation in a nerve comprises a housing that is shaped so as to define a chamber, one wall of which is defined by a membrane that separates the chamber from the outside of the housing. An interior of the chamber is in fluid communication with the nerve. The assembly further comprises at least a first electrode, which is positioned within the chamber, and at least a second electrode, which is positioned outside of the housing, e.g., in a vicinity of the membrane. A control unit is configured to drive a current between the electrodes such that the first electrode has a positive charge, and the second electrode has a negative charge. As a result, the pH of the medium in the chamber increases, and the pH of the medium outside the chamber decreases. The higher pH in the chamber inhibits action potentials traveling in the nerve past the chamber.

In some embodiments of the present invention, an assembly comprises at least one substance-dispensing element, and, for some applications, at least one cathode, which are fixed to a housing. The substance-dispensing unit contains a substance, and is configured to dispense the substance to a nerve. For some applications, the substance comprises a drug capable of blocking action potential propagation. For some applications, a control unit is configured to drive the cathode to apply a current to the nerve that generates action potentials traveling in first and second directions in the nerve. The substance-dispensing element releases the drug, thereby blocking propagation of the cathode-generated action potentials traveling in the second direction. As a result, the assembly generates unidirectional action potentials in the nerve traveling in the first direction.

In some embodiments of the present invention, a system for iontophoretically administering a substance to a nerve comprises an assembly comprising a housing that is shaped so as to define at least first and second chambers which surround respective first and second portions of the nerve. The first chamber contains a solid or liquid containing the substance, and the second chamber typically contains a liquid without the substance. The assembly further comprises at least first and second electrodes, which are positioned within the first and second chambers, respectively. A control unit is configured to drive a current between the electrodes that iontophoretically drives the substance from the first chamber into the nerve.

There is therefore provided, in accordance with an embodiment of the present invention, apparatus including:

an assembly, which includes a housing configured to be applied to a nerve of a subject, and at least one cathode and at least one Peltier cooler, which are fixed to the housing; and a control unit, which is configured to drive:

the cathode to apply an activating current to the nerve that generates action potentials traveling in first and second directions in the nerve, and the Peltier cooler to cool the nerve sufficiently to block propagation of at least a portion of the cathode-generated action potentials traveling in the second direction.

In an embodiment, the control unit is configured to drive the Peltier cooler to cool the nerve sufficiently to block the propagation of substantially all of the cathode-generated action potentials traveling in the second direction.

For some applications, the assembly includes a temperature sensor, positioned in a vicinity of the Peltier cooler, and the control unit is configured to set at least one parameter responsively to the sensed temperature, the parameter selected from the group consisting of: a parameter of the activating current, and a parameter of the cooling.

For some applications, the nerve includes a vagus nerve, the assembly is configured to be applied to the vagus nerve, and the control unit is configured to drive the cathode to generate the action potentials sufficient to reduce a heart rate of the subject.

In an embodiment, the control unit is configured to drive the Peltier cooler not in coordination with the driving of the cathode.

In an embodiment, the nerve contains smaller- and larger-diameter fibers, and the control unit is configured to drive the Peltier cooler to cool the nerve sufficiently to block the propagation of the portion of the cathode-generated action potentials traveling in the smaller-diameter fibers. For some applications, the control unit is configured to drive the Peltier cooler to apply cooling substantially constantly while blocking the propagation of the portion of the cathode-generated action potentials traveling in the smaller-diameter fibers. For some applications, the Peltier cooler includes a first Peltier cooler, the assembly includes a second Peltier cooler fixed to the housing such that the cathode is longitudinally between the first and second Peltier coolers, and the control unit is configured to drive the second Peltier cooler to cool the nerve sufficiently to block propagation of at least a portion of the cathode-generated action potentials traveling in the first direction. For some applications, the assembly includes an anode fixed to the housing such that the cathode is longitudinally between the anode and the Peltier cooler, and the control unit is configured to drive the anode to apply an inhibiting current to the nerve that blocks propagation of at least a portion of the cathode-generated action potentials traveling in the first direction.

In an embodiment, the assembly includes at least one anode, and the control unit is configured to drive the anode to apply an inhibiting current to the nerve that blocks the propagation of a portion of the cathode-generated action potentials traveling in the second direction. In an embodiment, the control unit is configured to drive the anode not in coordination with the driving of the cathode. For some applications, the nerve contains smaller-, intermediate-, and larger-diameter fibers, and the control unit is configured to: configure the inhibiting current to block the propagation of the portion of the cathode-generated action potentials traveling in the larger-diameter fibers, and drive the Peltier cooler to cool the nerve sufficiently to block the propagation of the portion of the cathode-generated action potentials traveling in the smaller-diameter fibers.

For some applications, the Peltier cooler includes a first Peltier cooler, the assembly includes a second Peltier cooler fixed to the housing such that the cathode is longitudinally between the first and second Peltier coolers, and the control unit is configured to drive the second Peltier cooler to cool the nerve sufficiently to block propagation of at least a portion of the cathode-generated action potentials traveling in the first direction.

For some applications, the anode includes a first anode and the inhibiting current includes a first inhibiting current, the assembly includes a second anode fixed to the housing such that the cathode is longitudinally between the second anode, on the one hand, and the first anode and the Peltier cooler, on the other hand, and the control unit is configured to drive the second anode to apply a second inhibiting current to the nerve that blocks propagation of at least a portion of the cathode-generated action potentials traveling in the first direction.

In an embodiment, the control unit is configured to configure the activating current to generate the action potentials in fibers of the nerve up to a first depth from a surface of the nerve, and drive the Peltier cooler to cool fibers of the nerve up to a second depth less than the first depth, thereby blocking the propagation of the cathode-generated action potentials traveling in the second direction in the fibers of the nerve up to the second depth. For some applications, the first depth is substantially equal to a radius of the nerve, and the control unit is configured to configure the activating current to generate the action potentials in the fibers of the nerve at substantially all depths. For some applications, the Peltier cooler includes a first Peltier cooler, the assembly includes a second Peltier cooler fixed to the housing such that the cathode is longitudinally between the first and second Peltier coolers, and the control unit is configured to drive the second Peltier cooler to cool the nerve sufficiently to block propagation of at least a portion of the cathode-generated action potentials traveling in the first direction. For some applications, the control unit is configured to drive the Peltier cooler to applying cooling to the nerve in a series of pulses having an average duration of less than 5 seconds.

There is further provided, in accordance with an embodiment of the present invention, apparatus including:
an assembly, which includes:
a housing configured to be applied to a nerve of a subject, the housing shaped so as to define a chamber, an interior of which is in fluid communication with the nerve when the housing is applied to the nerve, wherein at least one wall of the chamber includes a membrane that separates the interior of the chamber from a region outside the chamber;
at least a first electrode, which is positioned within the chamber; and
at least a second electrode, which is positioned in the region outside the chamber, in a vicinity of the membrane; and
a control unit, which is configured to:
drive a current between the first and second electrodes such that the first electrode has a positive charge, and the second electrode has a negative charge; and
configure the current to increase a pH in the interior of the chamber sufficiently to inhibit action potentials traveling in the nerve past the chamber.

In an embodiment, the region outside the chamber is outside the housing, and the housing is configured such that the membrane separates the interior of the chamber from the region outside the housing.

For some applications, the assembly includes a pH sensor, which is configured to sense a pH within the chamber, and the control unit is configured to set at least one parameter of the current responsively to the sensed pH.

For some applications, the nerve includes a sympathetic nerve that innervates a heart of the subject, the housing is configured to be applied to the sympathetic nerve, and the control unit is configured to drive the current to increase the pH to inhibit the action potentials sufficiently to reduce a rate of the heart.

In an embodiment, the control unit is configured to drive the current substantially continuously for a period of time that is greater than one minute.

In an embodiment, the control unit is configured to drive the current substantially continuously for a period of time that is greater than one hour.

In an embodiment, the control unit is configured to generate an increased level of sodium and hydroxide ions inside the chamber by driving the current.

In an embodiment, the control unit is configured to inhibit action potentials traveling in the nerve past the chamber by facilitating diffusion of the sodium and the hydroxide ions into the nerve.

In an embodiment, the control unit is configured to generate an increased level of hydrogen and chloride ions in a vicinity of the second electrode by driving the current.

In an embodiment, the membrane is configured to separate (a) the sodium and the hydroxide ions, from (b) the hydrogen and the chloride ions.

In an embodiment, the current includes a first current, the assembly includes at least one cathode, and the control unit is configured to drive the cathode to apply a second current to the nerve that generates action potentials traveling in first and second directions in the nerve, and configure the first current to increase the pH sufficiently to block propagation past the chamber of at least a portion of the cathode-generated action potentials traveling in the second direction. For some applications, the control unit is configured to drive the cathode to apply the second current by driving the second current between the cathode and at least one of the first and second electrodes. For some applications, the nerve includes a vagus nerve, the assembly is configured to be applied to the vagus nerve, and the control unit is configured to drive the cathode to generate the action potentials sufficiently to reduce a heart rate of the subject. In an embodiment, the control unit is configured to drive the first current between the first and second electrodes, not in coordination with the driving of the cathode.

In an embodiment, the chamber includes a first chamber, and the interior of the chamber includes a first interior of the first chamber, the housing is shaped so as to define a second chamber longitudinally adjacent to the first chamber, a second interior of which is in fluid communication with the nerve when the housing is applied to the nerve, and includes the region outside the first chamber, and the housing is configured such that the membrane separates the first interior of the first chamber from the second interior of the second chamber. For some applications, the membrane includes a first membrane; the housing is shaped so as to define a third chamber longitudinally adjacent to the first chamber, a third interior of which is in fluid communication with the nerve when the housing is applied to the nerve; and at least one wall of the third chamber includes a second membrane that separates the third interior from the first interior of the first chamber.

For some applications, the control unit is configured to set the current to have an amplitude of at least 10 mA, e.g., at least 50 mA.

There is still further provided, in accordance with an embodiment of the present invention apparatus including an assembly, which includes:

a housing configured to be applied to a nerve of a subject; and a substance-dispensing element, fixed to the housing, the element including a substance, and configured to dispense the substance to the nerve.

For some applications, the assembly includes a reservoir, which contains at least a portion of the substance, and the substance-dispensing element is in fluid communication with the reservoir. For some applications, the substance-dispensing element includes a polymer containing the substance.

In an embodiment, the substance-dispensing element is configured to actively dispense the substance.

In an embodiment, the apparatus includes a control unit, the housing is shaped so as to define at least first and second chambers, which are configured to surround respective first and second portions of the nerve when the housing is applied to the nerve, the first chamber contains the substance, the assembly includes first and second electrodes, positioned within the first and second chambers, respectively, and the control unit is configured to drive a current between the first and second electrodes that iontophoretically drives the substance into the nerve.

In an embodiment, the substance is selected from the group consisting of: a drug, genes, and cells.

In an embodiment, the substance-dispensing element is configured to passively dispense the substance. For example, the substance-dispensing element may be configured to passively dispense the substance by osmosis.

In an embodiment, the substance-dispensing element includes a membrane permeable to the substance, which membrane: (a) together with an inner surface of the housing, defines a chamber for containing the substance, and (b) together with lateral portions of the housing, defines a space that is in fluid communication with the nerve when the housing is applied to the nerve. For some applications, the apparatus includes a control unit, and the substance-dispensing element includes: at least a first electrode, which is positioned within the chamber; and at least a second electrode, which is positioned within the space, and the control unit is configured to drive a current between the first and second electrodes that iontophoretically drives the substance from the chamber to the space. For some applications, the substance-dispensing element is configured such that the substance crosses the membrane from the chamber to the space by osmosis.

In an embodiment, the substance includes a substance capable of blocking action potential propagation. For some applications, the substance may be selected from the group consisting of: morphine, lidocaine, Botulinum Toxin Type A, a steroid, a hormone, and an ion-channel blocking substance. For some applications, the nerve includes a sympathetic nerve that innervates a heart of the subject, the housing is configured to be applied to the sympathetic nerve, and the substance-dispensing element is configured to dispense an amount of the substance sufficient to reduce a rate of the heart.

For some applications, the apparatus includes: at least one cathode, fixed to the housing; and a control unit, which is configured to drive the cathode to apply a current to the nerve that generates action potentials traveling in first and second directions in the nerve, and the substance-dispensing element is configured to dispense a quantity of the substance sufficient to block propagation of substantially all of the cathode-generated action potentials traveling in the second direction. For some applications, the assembly includes a Peltier cooler, fixed to the housing, and the control unit is configured to drive the Peltier cooler to cool the nerve sufficiently to block propagation of at least a portion of the cathode-generated action potentials traveling in the nerve.

There is additionally provided, in accordance with an embodiment of the present invention, apparatus including:

an assembly, which includes:
a housing configured to be applied to a nerve of a subject;
at least one cathode, fixed to the housing; and
a heating element fixed to the housing in a vicinity of the cathode; and
a control unit, which is configured to drive:
the cathode to apply a current to the nerve, and
the heating element to apply, to the nerve, heat insufficient to cause damage to the nerve.

For some applications, the assembly includes an element that serves as both the cathode and the heating element. For some applications, the assembly includes a temperature sensor, positioned in a vicinity of the cathode, and the control unit is configured to set at least one parameter responsively to the sensed temperature, the parameter selected from the group consisting of: a parameter of the current, and a parameter of the applied heat.

For some applications, the nerve includes a vagus nerve, the assembly is configured to be applied to the vagus nerve, and the control unit is configured to drive the cathode to apply the current to generate action potentials sufficiently to reduce a heart rate of the subject.

There is still additionally provided, in accordance with an embodiment of the present invention, apparatus including:

an assembly which includes:
at least a first electrode configured to penetrate an epineurium of a nerve; and
at least a second electrode configured to remain outside the epineurium; and
a control unit, configured to drive a current between the first and second electrodes, and to configure the current to pump positive ions away from an area surrounding an axon of the nerve, through the epineurium, in order to reduce a positive charge of the area.

For some applications, the first electrode is shaped as a needle electrode. For some applications, the control unit is configured to apply a DC signal between the electrodes.

There is also provided, in accordance with an embodiment of the present invention, apparatus including:

a temperature modulation unit, configured to be applied to a ganglion of a subject; and
a control unit, configured to drive the temperature modulation unit to modulate a temperature of the ganglion sufficiently to affect a level of activity of the ganglion.

For some applications, the apparatus includes a stimulation element, and the control unit is configured to drive the stimulation element to apply stimulation to the ganglion in conjunction with driving the temperature modulation unit to modulate the temperature of the ganglion, the stimulation selected from the group consisting of: activating stimulation, and inhibiting stimulation.

In an embodiment, the temperature modulation unit includes a heating element.

For some applications, the ganglion includes a sphenopalatine ganglion (SPG), and the temperature modulation unit is configured to be applied to the SPG.

In an embodiment, the temperature modulation unit includes at least one Peltier cooler. For some applications, the control unit drives the Peltier cooler to cool the ganglion. Alternatively or additionally, the control unit drives the Peltier cooler to heat the ganglion. For some applications, the control unit is configured to drive the Peltier cooler by applying a current to the Peltier cooler, and setting a direction of the current to set whether the Peltier cooler cools or heats the ganglion. For some applications, the apparatus includes a sensor configured to sense a physiological parameter of the subject, and the control unit is configured to set the direction of the current at least in part responsively to the sensed physiological parameter.

There is further provided, in accordance with an embodiment of the present invention, apparatus including:

at least one Peltier cooler, configured to be applied to tissue of a heart; and a control unit, configured to drive the Peltier cooler to cool the tissue sufficiently to slow a rate of the heart.

In an embodiment, the tissue includes an AV node of the heart, and the Peltier cooler is configured to be applied to the AV node.

There is still further provided, in accordance with an embodiment of the present invention, a method including:

applying, to a nerve of a subject, an activating current that generates action potentials traveling in first and second directions in the nerve; and Peltier-cooling the nerve sufficiently to block propagation of at least a portion of the action potentials traveling in the second direction.

For some applications, the method includes identifying that the subject suffers from a condition selected from the group consisting of: Parkinson's disease, erectile dysfunction, premature ejaculation, tinnitus, obesity, heart failure, and cerebral palsy, and applying the activating current and Peltier-cooling the nerve include applying the activating current and Peltier-cooling the nerve responsively to the identifying.

There is additionally provided, in accordance with an embodiment of the present invention, a method including:

placing a housing in a vicinity of a nerve of subject such that an interior of a chamber defined by the housing is in fluid communication with the nerve, wherein at least one wall of the chamber includes a membrane that separates the interior of the chamber from a region outside the chamber;

driving a current between a first site within the chamber and a second site in a region outside the chamber, which second site is in a vicinity of the membrane; and configuring the current to increase a pH in the interior of the chamber sufficiently to inhibit action potentials traveling in the nerve past the chamber.

There is yet additionally provided, in accordance with an embodiment of the present invention, a method including:

implanting, at a nerve of a subject, a substance-dispensing element containing a substance; and dispensing the substance to the nerve from the element.

There is still additionally provided, in accordance with an embodiment of the present invention, a method including:

applying, at a cathodic site, a cathodic current to a nerve of a subject; and applying, to the nerve in a vicinity of the cathodic site, heat that is insufficient to cause damage to the nerve.

There is also provided, in accordance with an embodiment of the present invention, a method including:

driving a current between first and second sites, the first site within an epineurium of a nerve, and the second site outside the epineurium; and configuring the current to pump positive ions away from an area surrounding an axon of the nerve, through the epineurium, in order to reduce a positive charge of the area.

There is further provided, in accordance with an embodiment of the present invention, a method including:

applying a temperature modulation unit to a ganglion of a subject; and driving the temperature modulation unit to modulate a temperature of the ganglion sufficiently to affect a level of activity of the ganglion.

There is still further provided, in accordance with an embodiment of the present invention, a method including:

applying at least one Peltier cooler to tissue of a heart; and driving the Peltier cooler to cool the tissue sufficiently to slow a rate of the heart.

The present invention will be more fully understood from the following detailed description of embodiments thereof, taken together with the drawings, in which:

BRIEF DESCRIPTION OF THE DRAWINGS

FIGS. 6-7 are schematic illustrations of substance-dispensing elements of the system of FIG. 5, in accordance with respective embodiments of the present invention;

FIG. 8 is a schematic cross-sectional illustration of a system for iontophoretically administering a substance to a nerve, in accordance with an embodiment of the present invention;

FIGS. 9-11 are schematic illustrations of systems for generating unidirectional action potentials in a nerve, in accordance with respective embodiments of the present invention; and FIG. 12 is a schematic illustration of another system for stimulating a nerve, in accordance with an embodiment of the present invention.

DETAILED DESCRIPTION OF EMBODIMENTS

Figure 1:
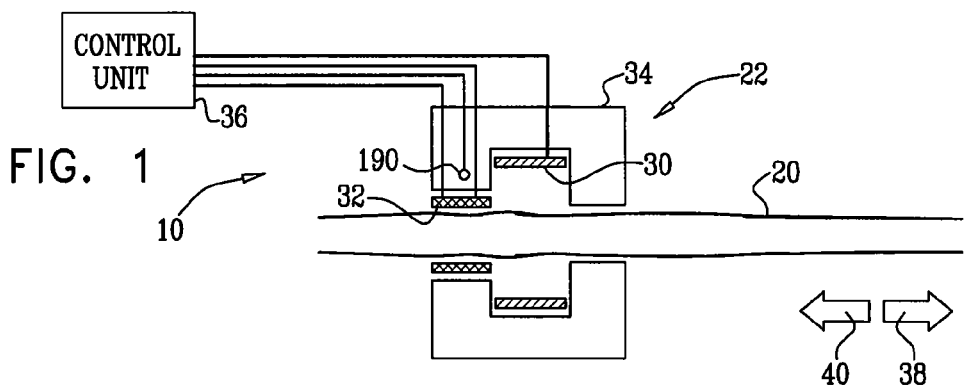
FIGS. 1-5 are schematic illustrations of systems for stimulating a nerve, in accordance with respective embodiments of the present invention.

FIG. 1 is a schematic illustration of a system 10 for stimulating a nerve 20, in accordance with an embodiment of the present invention. System 10 comprises an assembly 22, which comprises at least one cathode 30 and at least one Peltier cooler 32, which are fixed to a housing 34. The system further comprises a control unit 36, which is configured to drive: (a) cathode 30 to apply a current to nerve 20 that generates action potentials traveling in first and second directions 38 and 40 in the nerve, and (b) Peltier cooler 32 to cool the nerve, thereby blocking propagation of the cathode-generated action potentials traveling in second direction 40. As a result, assembly 22 generates unidirectional action potentials in the nerve traveling in first direction 38. For some applications, assembly 22 comprises at least one anode, while for other applications, at least one anode remote from the assembly is provided, e.g., control unit 36 serves as the anode.

It is noted that, for some applications, control unit 36 is configured to drive Peltier cooler 32 (and other Peltier coolers described herein) to cool the nerve, not in coordination with the generation of the action potentials. For example, the control unit may be configured to apply cooling substantially constantly over a designated time period (e.g., seconds, minutes, or hours), in order to block the propagation of the cathode-generated action potentials. In some embodiments, the Peltier cooler is used to block action potentials which are not generated by the control unit, for example, to block naturally-induced action potentials.

Figure 2:
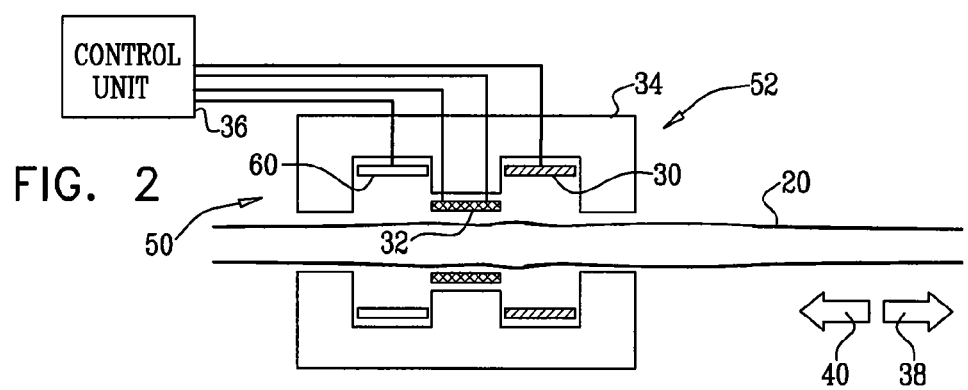

Reference is made to FIG. 2, which is a schematic illustration of a system 50 for stimulating nerve 20, in accordance with an embodiment of the present invention. System 50 comprises an assembly 52, which comprises at least one cathode 30, at least one anode 60, and at least one Peltier cooler 32, which are fixed to housing 34. Although Peltier cooler 32 is shown in the figure as being positioned between cathode 30 and anode 60, for some applications the anode is positioned between the cathode and the Peltier cooler.

Control unit 36 is configured to drive: (a) cathode 30 to apply a current to nerve 20 that generates action potentials traveling in first and second directions 38 and 40 in the nerve, (b) anode 60 to apply an inhibiting current to nerve 20 that partially blocks propagation of the cathode-generated action potentials traveling in second direction 40, and (c) Peltier cooler 32 to block propagation of the cathode-generated action potentials traveling in second direction 40. As a result, system 50 generates unidirectional action potentials in the nerve traveling in first direction 38.

It is noted that, for some applications, control unit 36 is configured to drive anode 60 (and other action-potential-blocking electrodes described herein) to apply the inhibiting current, not in coordination with the generation of the action potentials. For example, the control unit may be configured to drive the anode to apply the inhibiting current substantially constantly over a designated time period (e.g., seconds, minutes, or hours), in order to block the propagation of the cathode-generated action potentials. In some embodiments, the anode is used to block action potentials which are not generated by the control unit, for example, to block naturally-induced action potentials.

Reference is again made to FIG. 1. In an embodiment of the present invention, control unit 36 is configured to drive:
  (a) cathode 30 to apply a current to nerve 20 that generates action potentials in fibers of the nerve up to a first depth from the surface of the nerve, and
  (b) Peltier cooler 32 to cool fibers of the nerve up to a second depth less than the first depth, thereby blocking propagation of the cathode-generated action potentials traveling in the fibers of the nerve up to the second depth.

As a result, the system generates action potentials only in fibers of the nerve located between the first and second depths. For some applications, the first depth equals substantially the radius of the nerve, such that cathode 30 generates action potentials in all fibers of the nerve, a portion of which are blocked by Peltier cooler 32. In order to block fibers only up to a certain depth, control unit 36 typically drives cooler 32 to apply the cooling in a series of pulses having a short average duration, such as between about 1 and about 5 seconds. Alternatively, the pulses have a duration that is less than 1 second or greater than 5 seconds. For some applications, such pulses are applied with a duty cycle of between about 5% and about 50%. For example, if the pulses have a duration of 2 seconds and are applied with a duty cycle of 10%, 18-second non-cooling periods are provided between successive cooling pulses. Alternatively, the duty cycle is less than 5% or greater than 50%.

In this embodiment, system 10 typically generates selective-depth action potentials traveling in second direction 40. For some applications, assembly 22 further comprises at least one second anode and/or at least one second Peltier cooler, which the control unit drives to block cathode-generated action potentials traveling in nerve 20 in first direction 38 (configuration not shown).

Figure 3:
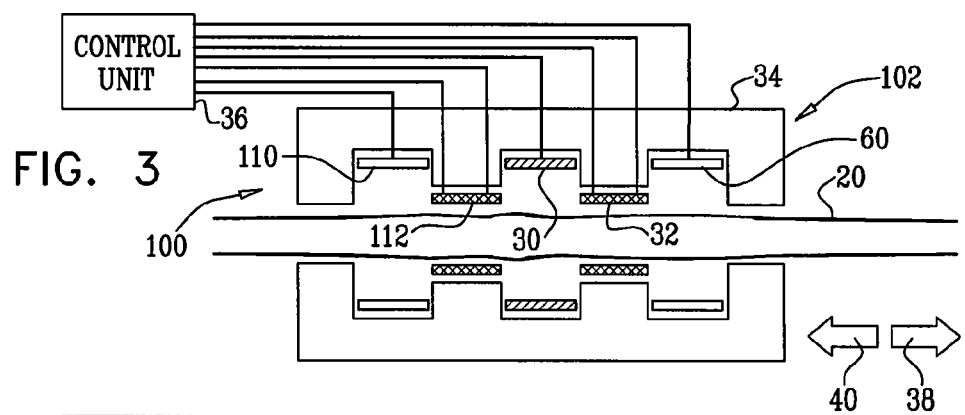

Reference is made to FIG. 3, which is a schematic illustration of a system 100 for applying current to nerve 20, in accordance with an embodiment of the present invention. System 100 comprises an assembly 102, which comprises at least one cathode 30, at least one anode 60, and at least one Peltier cooler 32, which are fixed to housing 34. Although Peltier cooler 32 is shown in the figure as being positioned between cathode 30 and anode 60, for some applications the anode is positioned between the cathode and the Peltier cooler.

Control unit 36 is configured to drive assembly 102 to selectively recruit nerve fibers of intermediate diameter, by:
  (a) driving cathode 30 to generate action potentials in fibers essentially of all diameters in first and second directions 38 and 40 in nerve 20,
  (b) driving anode 60 to inhibit the cathode-generated action potentials traveling in first direction 38 in larger-diameter fibers, and
  (c) driving the Peltier cooler to inhibit the cathode-generated action potentials traveling in first direction 38 in smaller-diameter fibers.

For some applications, assembly 102 further comprises at least one second anode 110 and/or at least one second Peltier cooler 112, which are positioned in housing 34 such that cathode 30 is between (a) anode 60 and Peltier cooler 32, on the one hand, and (b) second anode 110 and/or Peltier cooler 112, on the other hand. Control unit 36 is configured to drive second anode 110 and/or Peltier cooler 112 to block cathode-generated action potentials traveling in nerve 20 in second direction 40, as described hereinabove.

Figure 4:
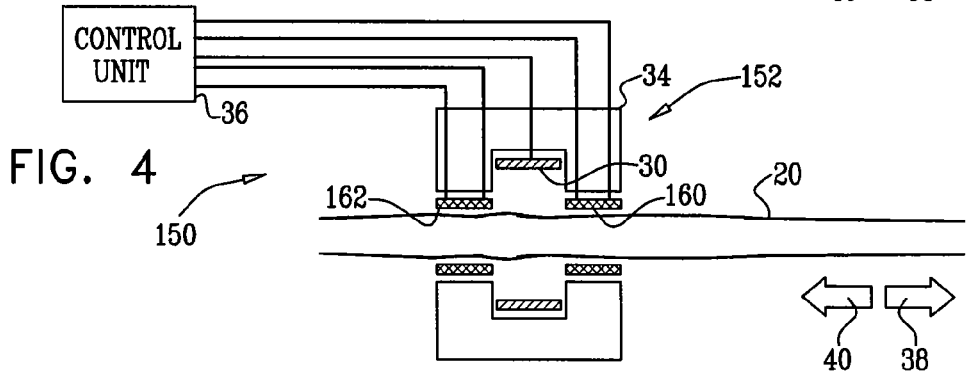

Reference is made to FIG. 4, which is a schematic illustration of a system 150 for stimulating nerve 20, in accordance with an embodiment of the present invention. System 150 comprises an assembly 152, which comprises at least first and second Peltier coolers 160 and 162, and at least one cathode 30 positioned between the coolers, all of which are fixed to housing 34. Control unit 36 is configured to drive cathode 30 to generate action potentials in nerve 20 traveling in both first and second directions 38 and 40. The control unit is configured to drive first cooler 160 to block substantially all of the cathode-generated action potentials traveling in first direction 38, and to drive second cooler 162 to block cathode-generated action potentials traveling in second direction 40 in fibers of the nerve up to a certain depth from the surface of nerve 20. As a result, system 150 generates selective-fiber depth unidirectional action potentials traveling in second direction 40. In order to block fibers only up to a certain depth, control unit 36 typically drives second cooler 162 to apply the cooling in a series of pulses having short average durations, such as between about 1 and about 5 seconds. Alternatively, the pulses have a duration that is less than 1 second or greater than 5 seconds. For some applications, the pulses are applied with a duty cycle, as described hereinabove.

Alternatively or additionally, control unit 36 drives second cooler 162 to block cathode-generated action potentials traveling in second direction 40 in smaller fibers of the nerve. As a result, assembly 152 generates selective-fiber-diameter unidirectional action potentials traveling in second direction 40. In order to perform such selective-fiber-diameter blocking, control unit 36 typically drives second cooler 162 to apply the cooling substantially constantly during the period in which it is desired to achieve such blocking. As the control unit decreases the temperature of the cooler, fibers having larger diameters are progressively blocked.

Figure 5:
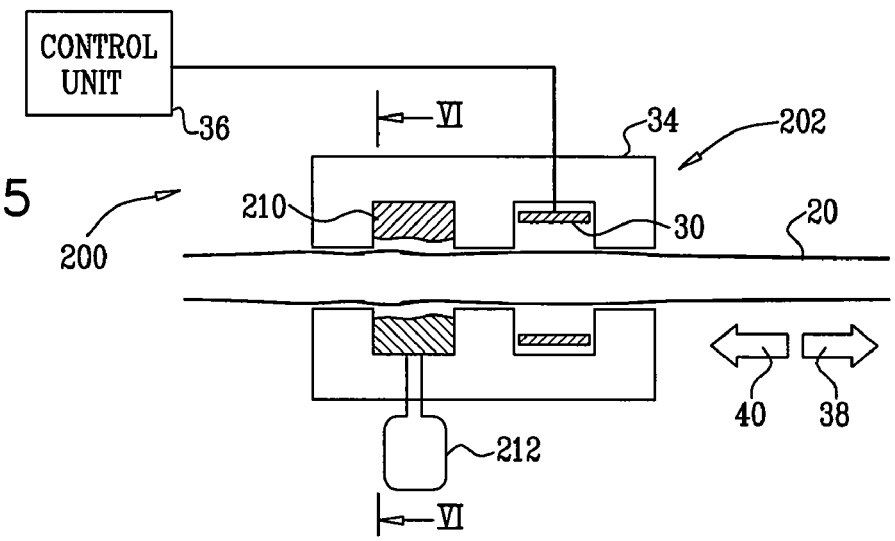

Reference is made to FIG. 5, which is a schematic illustration of a system 200 for stimulating nerve 20 and applying a substance thereto, in accordance with an embodiment of the present invention. System 200 comprises an assembly 202, which comprises at least one substance-dispensing element 210, and, for some applications, at least one cathode 30, which are fixed to housing 34. Alternatively, assembly 202 comprises only the at least one substance-dispensing element, and no electrodes. Substance-dispensing element 210 contains the substance, which, for some applications, comprises a drug. For some applications, the substance-dispensing element comprises a polymer containing the substance. For some applications, the element comprises a passive slow-release element, such as an osmotic pump, or an active substance-dispensing element, such as a mechanical pump. For some applications, substance-dispensing element 210 comprises a substance reservoir 212, for increasing the substance capacity of the element. For some applications, the substance-dispensing element contains a drug capable of blocking action potential propagation, such as morphine, lidocaine, Botox® (Botulinum Toxin Type A), a steroid, a hormone, or an ion-channel blocking drug.

For some applications, system 200 further comprises a control unit 36, which is configured to drive cathode 30 to apply a current to nerve 20 that generates action potentials traveling in first and second directions 38 and 40 in the nerve. Substance-dispensing element 210 releases the substance, thereby blocking propagation of the cathode-generated action potentials traveling in second direction 40. As a result, assembly 202 generates unidirectional action potentials in the nerve traveling in first direction 38. For some applications, assembly 202 comprises at least one anode, while for other applications, at least one anode remote from the assembly is provided, e.g., control unit 36 serves as the anode. For some applications, the released substance supplements action potential blocking effected by a Peltier cooler, as described hereinabove, and/or by application of current to the nerve.

It is noted that, for some applications, substance-dispensing element 210 is configured to release the substance not in coordination with the generation of the action potentials. For example, the substance-dispensing element may be configured to release the substance substantially constantly over a designated time period (e.g., seconds, minutes, or hours), in order to block the propagation of the cathode-generated action potentials. In some embodiments, the substance-dispensing element is used to block action potentials which are not generated by the control unit, for example, to block naturally-induced action potentials.

Figure 6:
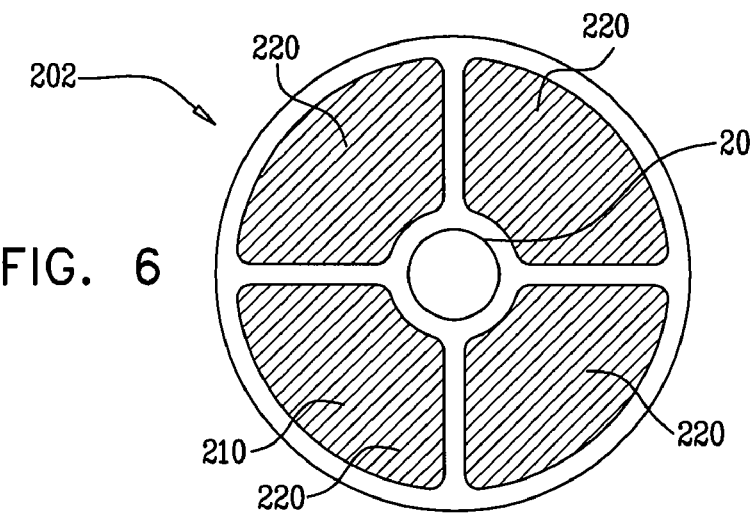

FIG. 6 is a schematic cross-sectional view of substance-dispensing element 210, in accordance with an embodiment of the present invention. In this embodiment element 210 comprises a plurality of substance-containing compartments 220, which contain either the same substance or different substances. Alternatively, substance-dispensing element 210 comprises a single substance-containing compartment that surrounds a portion of nerve 20, or substantially all of nerve 20 (configuration not shown in FIG. 6).

FIG. 7 is a schematic illustration of substance-dispensing element 210, in accordance with an embodiment of the present invention. In this embodiment, substance-dispensing element 210 comprises a membrane 230, which: (a) together with an inner surface of housing 34, defines a chamber 232 for containing the substance, and (b) together with nerve 20 and lateral portions of housing 34, defines a space 233 between the membrane and the nerve that is in fluid communication with the nerve. Substance-dispensing element 210 further comprises at least a first electrode 234, which is positioned within chamber 232 (e.g., on an inner surface of the chamber), and at least a second electrode 236, which is positioned between membrane 230 and the surface of nerve 20 (e.g., on an inner surface of a lateral portion of the housing). Control unit 34 is configured to drive a current between electrodes 234 and 236 that iontophoretically drives the substance from chamber 232 to space 233, from which the substance enters the nerve.

Reference is still made to FIG. 7. As mentioned above, for some applications, substance-dispensing element 210 element comprises an osmotic pump. For some applications, the osmotic pump comprises membrane 230, which, as described above, together with housing 34 defines substance-containing chamber 232 and space 233. In these applications, substance-dispensing element 210 does not comprise electrodes 234 and 236, but instead relies upon osmosis for the substance to cross membrane 230 from chamber 232 to space 233.

Reference is made to FIG. 8, which is a schematic cross-sectional illustration of a system 250 for iontophoretically administering a substance to nerve 20, in accordance with an embodiment of the present invention. System 250 comprises an assembly 252, which comprises housing 34. Housing 34 is shaped so as to define at least a first chamber 254 which surrounds a first portion of nerve 20, and at least a second chamber 256 which surrounds a second portion of the nerve. First chamber 254 contains a solid or liquid containing the substance, which, for some applications, comprises a drug, and second chamber 256 typically contains a liquid without the substance. Assembly 252 further comprises at least a first electrode 260, which is positioned within first chamber 254 (e.g., on an inner surface of the first chamber), and at least a second electrode 262, which is positioned within second chamber 256 (e.g., on an inner surface of the second chamber). Control unit 36 is configured to drive a current between electrodes 234 and 236 that iontophoretically drives the substance from first chamber 254 into nerve 20. Some of the substance (or other ions) subsequently passes into second chamber 256. For some applications, chamber 254 comprises a polymer that contains the substance. For some applications, the substance comprises a powder; liquid entering first chamber 254 wets the powder.

In some embodiments of the present invention, techniques described herein for administering a substance to nerve 20 are used for administering genes or cells (e.g., stem cells) to nerve 20 or to non-nervous tissue.

It is noted that, for some applications, system 250 is configured to drive the substance into nerve 20 not in coordination with the generation of action potentials by the control unit. For example, system 250 may be configured to drive the substance into the nerve substantially constantly over a designated time period (e.g., seconds, minutes, or hours), in order to block the propagation of cathode-generated action potentials. In some embodiments, system 250 is used to block action potentials which are not generated by the control unit, for example, to block naturally-induced action potentials.

Reference is made to FIG. 9, which is a schematic illustration of a system 300 for blocking action potentials traveling through a nerve 20, in accordance with an embodiment of the present invention. System 300 comprises an assembly 352, which comprises housing 34. The housing is shaped so as to define a chamber 356, one wall of which is defined by a membrane 358 that separates the chamber from the outside of the housing. An interior of chamber 356 is in fluid communication with nerve 20; for example, the chamber is open to the nerve, or is separated therefrom by another fluid-permeable membrane (not shown). Assembly 352 further comprises at least a first electrode 360, which is positioned within chamber 356 (e.g., on an inner surface of the chamber), and at least a second electrode 362, which is positioned outside of housing 34 in a vicinity of membrane 358.

The control unit is configured to drive a current between electrodes 360 and 362 such that electrode 360 has a positive charge, and electrode 362 has a negative charge. As a result, the pH of the medium in chamber 356 increases, and the pH of the medium outside the chamber decreases. The higher pH in the chamber inhibits action potentials traveling past the chamber in nerve 20. For some applications, in order to reverse this effect, the control unit reverses the polarity of the current. For some applications, assembly 352 comprises a pH sensor which is configured to sense a pH within chamber 356, and control unit 36 is configured to set at least one parameter of the current responsively to the sensed pH. For some applications, setting the at least one parameter comprises applying or withholding applying the current.

In some embodiments, assembly 352 comprises at least one cathode 354 fixed to housing 34, and, optionally, at least one additional electrode 355, such as an anode. Control unit 36 is configured to drive cathode 354 to apply a current to nerve 20 that generates action potentials traveling in first and second directions 38 and 40 in the nerve, as described hereinabove. As described hereinabove, the higher pH in chamber 356 inhibits action potentials traveling in nerve 20 in first direction 38 (i.e., past the chamber). As a result, system 300 generates unidirectional action potentials in the nerve traveling in second direction 40.

It is noted that some embodiments of the present invention describe inhibiting action potentials by increasing pH near the nerve. The scope of the present invention includes decreasing pH (e.g., at least by a threshold amount) in order to inhibit action potentials, as well.

Typically, hydroxide ions are attracted to electrode 360, due to the positive charge on electrode 360, resulting in an increased level of hydroxide ions inside chamber 356. The increased level of hydroxide ions inside chamber 356 increases the pH inside chamber 356. In some embodiments, sodium ions are attracted to the hydroxide ions, and there is an increased level of sodium ions inside chamber 356. The sodium and hydroxide ions inside chamber 356 diffuse into nerve 20, causing action potentials traveling through nerve 20 to be blocked.

Further typically, hydrogen ions are attracted to electrode 362, and there is an increased level of hydrogen ions in the vicinity of electrode 362. The hydrogen ions attract chloride ions, resulting in an increased level of chloride ions in the vicinity of electrode 362. Membrane 358 separates the hydrogen and chloride ions that are present in the vicinity of electrode 362, from the sodium and hydroxide ions that are present in the vicinity of electrode 360.

For some applications, control unit 36 configures the current driven between electrodes 360 and 362 to have a relatively high amplitude, which is typically greater than an amplitude that can be safely and/or regularly applied to nerve tissue. Such a high amplitude is possible because the current substantially does not travel through tissue of nerve 20. For example, the current may have an amplitude of greater than 10 mA or greater than 50 mA, e.g., between about 10 and 100 mA, such as between about 50 and about 100 mA.

For some applications, system 300 is configured to block action potentials traveling in nerve 20 which were not generated by the system. For these applications, the system typically does not comprise cathode 354, additional electrode 355, or the portion of housing 352, to which cathode 354 and electrode 355 are coupled. In some embodiments, system 300 modulates the pH inside chamber 356 irrespective of (i.e., not in coordination with) the generation of action potentials in nerve 20. For some applications, system 300 modulates the pH inside chamber 356 continuously for a given period of time, such as for more than a minute, or more than an hour. For example, system 300 may increase the pH inside the chamber for the duration of a time period during which a patient suffering from Parkinson's disease is undergoing a bout of tremors.

Reference is made to FIG. 10, which is a schematic illustration of a system 400 for blocking action potentials traveling through nerve 20, in accordance with an embodiment of the present invention. System 400 comprises an assembly 402, which comprises a housing 34. The housing is shaped so as to define at least first and second chambers 406 and 408, which are adjacent to one another along the nerve, and separated by a membrane 410. Respective interiors of the chambers are in fluid communication with nerve 20; for example, the chambers are open to the nerve, or are separated therefrom by a membrane (not shown). Assembly 402 further comprises at least a first electrode 412, which is positioned within first chamber 406 (e.g., on an inner surface of the first chamber), and at least a second electrode 414, which is positioned within second chamber 408 (e.g., on an inner surface of the second chamber).

Control unit 36 is configured to drive a current between electrodes 412 and 414 such that electrode 412 has a positive charge, and electrode 414 has a negative charge. As a result, the pH of the medium in chamber 406 increases, as described hereinabove with reference to chamber 356 of system 300. The pH of the medium in chamber 408 decreases, typically due to hydrogen ions being attracted to electrodes 414. The higher pH in chamber 406 inhibits action potentials traveling in nerve 20 as the action potentials pass first chamber 406. In some embodiments this is due to sodium and hydroxide ions that are present in chamber 406 diffusing into nerve 20, as described with reference to system 300. Membrane 410 typically separates sodium and hydroxide ions that are present in chamber 406, from hydrogen and chloride ions that are present in chamber 408.

For some applications, the housing is shaped so as to define at least a third chamber 416, which is adjacent to chamber 406 and separated therefrom by a membrane 418. The assembly further comprises at least a third negative electrode 420 positioned within third chamber 416 (e.g., on an inner surface of the third chamber).

In some embodiments, assembly 402 comprises at least one cathode 404 fixed to housing 34, and, optionally, at least one additional electrode 405, such as an anode. Control unit 36 is configured to drive cathode 404 to apply a current to nerve 20 that generates action potentials traveling in first and second directions 38 and 40 in the nerve. The increased pH inside chamber 406 blocks action potentials from traveling through nerve 20 in first direction 38, as they pass chamber 406. As a result, system 400 generates unidirectional action potentials in the nerve traveling in second direction 40.

For some applications, system 400 is configured to block action potentials traveling in nerve 20 which were not generated by the system, as described hereinabove with reference to system 300. For these applications, the system typically does not comprise cathode 404 additional electrode 405, or the portion of housing 34 to which cathode 404 and electrode 405 are coupled.

Reference is made to FIG. 11, which is a schematic illustration of a system 450 for generating and/or blocking action potentials in nerve 20, in accordance with an embodiment of the present invention. System 450 comprises an assembly 452, which comprises at least one cathode 454 fixed to housing 34. The housing is shaped so as to define at least first and second chambers 456 and 458, which are adjacent to one another along the nerve, and separated by a membrane 460. Respective interiors of the chambers are in fluid communication with nerve 20; for example, the chambers are open to the nerve, or are separated therefrom by a membrane (not shown). Assembly 452 further comprises at least a second electrode 462, which is positioned within first chamber 456 (e.g., on an inner surface of the first chamber), and at least a third electrode 464, which is positioned within second chamber 458 (e.g., on an inner surface of the second chamber).

Control unit 36 is configured to selectively perform one or both of the following, such as alternatingly, each of which is described in more detail hereinbelow: (a) inhibit action potentials traveling in nerve 20 past second chamber 458, by increasing the pH within second chamber 458, and/or (b) generate action potentials using cathode 454.

In order to inhibit action potentials traveling in nerve 20 past second chamber 458, the control unit is configured to drive a current between second and third electrodes 462 and 464 such that electrode 464 has a positive charge, and electrode 462 has a negative charge. As a result, the pH of the medium in chamber 458 increases, and the pH of the medium in chamber 456 decreases. The higher pH in chamber 458 inhibits action potentials traveling in nerve 20 as the action potentials pass second chamber 458, as described hereinabove.

In order to generate action potentials in nerve 20 using cathode 454, control unit 36 drives the cathode to apply a current to nerve 20, typically using second electrode 462 or third electrode 464 as an anode. Alternatively, assembly 452 comprises another electrode that serves as the anode, or system 450 comprises an anode located in a vicinity of cathode 454, or remotely therefrom, such as coupled to control unit 36.

For some applications, control unit 36 is configured to alternatingly: (a) drive cathode 454 to apply a current to nerve 20 that generates action potentials traveling in first and second directions 38 and 40 in the nerve, and (b) drive second and third electrodes 462 and 464 to increase the pH in chamber 458, thereby inhibiting action potentials traveling in nerve 20 in first direction 38 as the action potentials pass first chamber 458. As a result, system 450 generates unidirectional action potentials in the nerve traveling in second direction 40.

In an embodiment of the present invention, techniques described herein are used for treating Parkinson's disease. For example, the techniques described herein may be used to block nerve fibers that are conveying signals that induce tremor (e.g., to block efferent signals originating in the brain). Alternatively or additionally, the techniques described herein are used in combination with techniques described in the U.S. Pat. No. 6,839,594, which is incorporated herein by reference, mutatis mutandis. For some applications, the systems described herein apply low-level white noise random stimulation towards the affected limb, optionally in combination with the action potential blocking techniques described herein.

In an embodiment of the present invention, techniques are provided for treating erectile dysfunction and/or premature ejaculation, optionally using the nerve stimulation techniques described hereinabove. For some applications, at least one of the pudendal nerve, cavernous nerve, or sacral nerve is stimulated to support erection, and/or blocked to inhibit premature ejaculation. Optionally, such stimulation is unidirectional. For some applications, at least one the above-mentioned nerves is blocked to inhibit premature ejaculation, and a drug is administered to support erection, such as sildenafil. For some applications, at least one the above-mentioned nerves is blocked to inhibit premature ejaculation, and the endothelium of a blood vessel supplying blood to the penis is stimulated. Such blood vessels include the penile artery and the dorsal penile artery. For some applications, such stimulation is configured to increase release of nitric oxide. Such stimulation provides increased blood flow to a corpus cavernosum and/or a corpus spongiosum of the penis, thereby enabling an erection.

In an embodiment of the present invention, techniques described herein for blocking action potentials are used for controlling tinnitus, optionally in combination with a cochlear implant.

In an embodiment of the present invention, techniques described hereinabove for blocking action potentials are used to reduce stomach contractions, in order to treat obesity.

In an embodiment of the present invention, nerve stimulation techniques described hereinabove are used to reduce heart rate by blocking a sympathetic nerve, or by unidirectionally stimulating the vagus nerve in an efferent direction. For some applications, such techniques are used for treating heart failure.

Reference is made to FIG. 12, which is a schematic illustration of a system 500 for applying current to nerve 20, in accordance with an embodiment of the present invention. System 500 comprises an assembly 502, which comprises one or more anodes 504, e.g., at least two anodes 504 and at least one cathode 506 positioned between the anodes, which are fixed to housing 34. The assembly further comprises a heating element 508 positioned near the cathode. For some applications, the cathode is configured to serve as heating element 508. Control unit 36 drives cathode 506 and anodes 504 to apply a current to nerve 20, and drives heating element 508 to heat the nerve slightly without causing damage thereto. For example, heating element 508 may apply heat having a temperature of between about 37 and about 45 degrees C., e.g., between about 39 and about 42 degrees C. The applied heat causes increased sensitivity of smaller-diameter fibers within nerve 20 to the cathodic stimulation. As a result, system 500 recruits smaller-diameter fibers with lower applied current than would occur without the heating. Typically, the assembly selectively recruits nerve fibers beginning with smaller-diameter fibers, and progressively recruits larger-diameter fibers as the desired stimulation level increases, or, alternatively, recruits smaller- and larger-diameter fibers substantially equally as the desired stimulation level increases, rather than selectively recruiting larger-diameter fibers, as generally occurs when using conventional nerve stimulation techniques. Further alternatively, the assembly in any case recruits larger-diameter fibers earlier than smaller-diameter fibers, but the difference is less extreme than would be the case in the absence of the slight heating.

For some applications, this heating technique is combined with other stimulation and/or Peltier cooling techniques described herein. For some applications, assembly 502 comprises a temperature sensor 510, which is typically positioned in a vicinity of cathode 506. The measured temperature serves as feedback for control unit 36, which, responsively thereto, sets at least one parameter of the applied current and/or applied heat. For some applications, setting the parameter comprises applying or withholding applying the current and/or the heat.

In an embodiment of the present invention, system 10, 50, 100, 150, 200, 250, 300, 400, 450, or 500 comprises at least one physiological sensor, which is configured to measure a physiological property of the subject. The measured property serves as feedback for control unit 36, which, responsively thereto, sets at least one parameter of the applied stimulation. For example, the measured property may include a heart rate of the subject, a temperature of the subject, or pain. For some applications, the sensor comprises one or more electrodes fixed to assembly 34, and control unit 36 measures a level of nerve stimulation using the sensing electrodes. Alternatively or additionally, one or more of the cathodes or anodes of the assembly serve as a sensing electrode a portion of the time. For some applications, the system comprises an input element, which is configured to receive feedback manually entered by the subject, such as an indication of a level of pain experienced by the subject.

Reference is again made to FIG. 1. In an embodiment of the present invention, assembly 22 comprises a temperature sensor 190, which is positioned in a vicinity of Peltier cooler 32. The measured temperature serves as feedback for control unit 36, which, responsively thereto, sets at least one parameter of the applied current and/or cooling. For some applications, setting the at least one parameter comprises withholding applying the current and/or the cooling. Although this embodiment has been described with reference to system 10 of FIG. 1, it is also applicable to the other systems described herein which comprise Peltier coolers.

For some applications, control unit 36 is configured to apply the current to nerve 20 in a series of pulses, and/or with a duty cycle.

In an embodiment of the present invention, an assembly for nerve stimulation is configured to pump positive ions away from the area surrounding an axon, through the epineurium, in order to reduce the positive charge of the area. For some applications, the assembly comprises at least a first electrode configured to penetrate the epineurium, and at least a second electrode configured to remain outside the epineurium. For example, the first electrode may be shaped as a needle electrode. A control unit drives a current between the first and second electrodes, and configures the current to pump positive ions away from the area surrounding the axon. For example, the control unit may apply a DC signal between the electrodes.

In some embodiments of the present invention, the electrodes and Peltier coolers are typically configured to surround all or a portion of the nerve, such as at least 90 degrees, at least 180 degrees, at least 270 degrees, or substantially 360 degrees of the nerve. For example, the electrodes and Peltier coolers may be annularly shaped. Alternatively, for some applications, some of the electrodes and/or Peltier coolers described herein comprise a set of individually-activatable electrodes and/or coolers arranged around all or a portion of the nerve. For some applications, only a portion of the electrodes and/or coolers of a given set are activated, so as to activate and/or block only a certain circumferential portion of the nerve. For example, a calibration procedure may be performed to determine which portion of the electrodes and/or coolers to activate. For other applications, different ones of the electrodes and/or coolers are activated at different times. For some applications, one or more Peltier coolers are configured to block around substantially the entire nerve, and a portion of the electrodes are selectively activated to stimulate a portion of the nerve, e.g., a portion generally within a designated distance from the surface of the nerve, and/or a portion generally located within a designated circumferential portion of the nerve (for example, axons located between 90 and 120 degrees).

In an embodiment of the present invention, one or more of Peltier coolers 32, 112, 160, or 162, described hereinabove, are configured to at least partially penetrate nerve 20, rather than be positioned in a vicinity of or against an outer surface of the nerve.

In an embodiment of the present invention, techniques described herein are used for treating Parkinson's disease. For example, the techniques described herein may be used to block nerve fibers that are conveying signals that induce tremor (e.g., to block efferent signals originating in the brain). Alternatively or additionally, the techniques described herein are used in combination with techniques described in the above-mentioned U.S. Pat. No. 6,839,594, mutatis mutandis. For some applications, the systems described herein apply low-level white noise random stimulation towards the affected limb, optionally in combination with the action potential blocking techniques described herein.

In an embodiment of the present invention, techniques are provided for treating erectile dysfunction and/or premature ejaculation, optionally using the nerve stimulation techniques described hereinabove. For some applications, at least one of the pudendal nerve, cavernous nerve, or sacral nerve is stimulated to support erection, and/or blocked to inhibit premature ejaculation. Optionally, such stimulation is unidirectional. For some applications, at least one the above-mentioned nerves is blocked to inhibit premature ejaculation, and a drug is administered to support erection, such as sildenafil. For some applications, at least one the above-mentioned nerves is blocked to inhibit premature ejaculation, and the endothelium of a blood vessel supplying blood to the penis is stimulated. Such blood vessels include the penile artery and the dorsal penile artery. For some applications, such stimulation is configured to increase release of nitric oxide. Such stimulation provides increased blood flow to a corpus cavernosum and/or a corpus spongiosum of the penis, thereby enabling an erection.

In an embodiment of the present invention, techniques described herein for blocking action potentials are used for controlling tinnitus, optionally in combination with a cochlear implant.

In an embodiment of the present invention, techniques described hereinabove for blocking action potentials are used to reduce stomach contractions, in order to treat obesity.

In an embodiment of the present invention, nerve stimulation techniques described hereinabove are used to reduce heart rate by blocking a sympathetic nerve, or by unidirectionally stimulating the vagus nerve in an efferent direction. For some applications, such techniques are used for treating heart failure.

In an embodiment of the present invention, apparatus for pacing a heart comprises a Peltier cooler and a control unit. The Peltier cooler is configured to be applied to tissue of the heart, typically the AV node. The control unit drives the Peltier cooler to cool the tissue, so as to slow the heart. For some applications, techniques of this embodiment are combined with techniques described in the above-mentioned U.S. Pat. No. 5,876,422.

In an embodiment of the present invention, techniques described hereinabove for blocking action potentials are used to treat cerebral palsy by blocking sensory signals that induce spasms.

In an embodiment of the present invention, techniques described herein are used for activating and/or blocking a sympathetic nerve or a parasympathetic nerve.

In an embodiment of the present invention, apparatus for modulating a ganglion comprises a temperature modulation element and a control unit. The temperature modulation element is configured to be applied to the ganglion, and the control unit is configured to drive the temperature modulation unit to modulate the temperature of the ganglion in order to affect a level of activity of the ganglion. For some applications, the temperature modulation unit comprises a Peltier element, and the control unit drives the Peltier element to cool or heat the ganglion. For some applications, the control unit is configured to set the direction of the current driven through the Peltier element, in order to set whether the Peltier element cools or heats the ganglion. For example, the control unit may make such a determination responsively to a measured physiological parameter of the subject, or another signal received by the control unit. Alternatively, for some applications, the temperature modulation unit comprises a non-Peltier heating element, as is known in the art. For some applications, the apparatus further comprises a stimulation element, which may comprise one or more electrodes or an electromagnetic stimulator, and the control unit is configured to drive the stimulation element to stimulate (either to activate or to inhibit) the ganglion, and the temperature modulation unit to cool or heat the ganglion. For some applications, such combined stimulation and temperature modulation causes increased ganglionic output, and/or more controllable ganglionic output. For some applications, the ganglion includes the sphenopalatine ganglion (SPG).

Typically, the electrodes described herein comprise a material suitable for minimizing the potential difference at the interface with the tissue. For example, the electrodes may comprise titanium iridium, or Ag—AgCl.

Control units provided in embodiments of the present invention may have varying degrees of complexity. For some applications, the control units comprise circuitry that actively drives elements of the systems, while for other applications, the control units may comprise only one or a few elements, such as only a battery or other power source.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. For example, the different techniques for inhibiting action potentials may be combined or substituted for one another, e.g., the pH-based action potential inhibiting techniques described hereinabove with reference to FIG. 9 may be used instead of or in addition to the Peltier cooler inhibition techniques used in some embodiments of the present invention.

The invention claimed is:

1. Apparatus comprising:
an assembly, said assembly comprising:
a housing configured to be applied to a nerve of a subject, the housing shaped to define a chamber, an interior of said chamber being in fluid communication with the nerve when the housing is applied to the nerve, wherein at least one wall of the chamber comprises a membrane that separates the interior of the chamber from a region outside the chamber;
at least a first electrode, which is positioned within the chamber; and
at least a second electrode, which is positioned in the region outside the chamber, in a vicinity of the membrane; and
a control unit, which is configured to:
drive a current between the first and second electrodes such that the first electrode has a positive charge, and the second electrode has a negative charge, and
the control unit further configured to: configure the current to increase a pH in the interior of the chamber in order to inhibit action potentials traveling in the nerve past the chamber.

2. The apparatus according to claim 1,
wherein the current includes a first current,
wherein the assembly comprises at least one cathode, and
wherein the control unit is further configured to:
drive the cathode to apply a second current to the nerve that generates action potentials traveling in first and second directions in the nerve, and
configure the first current to increase the pH in order to block propagation past the chamber of at least a portion of the action potentials traveling in the second direction, and
drive the first current between the first and second electrodes, wherein the driving of the first current is not coordinated with the driving of the cathode.

3. The apparatus according to claim 1, wherein the control unit is configured to drive the current substantially continuously for a period of time that is greater than one minute.

4. The apparatus according to claim 3, wherein the control unit is configured to drive the current substantially continuously for a period of time that is greater than one hour.

5. The apparatus according to claim 1, wherein the control unit is configured to generate an increased level of sodium and hydroxide ions inside the chamber by driving the current.

6. The apparatus according to claim 5, wherein the control unit is configured to inhibit action potentials traveling in the nerve past the chamber by facilitating diffusion of the sodium and the hydroxide ions into the nerve.

7. The apparatus according to claim 5, wherein the control unit is configured to generate an increased level of hydrogen and chloride ions in a vicinity of the second electrode by driving the current.

8. The apparatus according to claim 7, wherein the membrane is configured to separate (a) the sodium and the hydroxide ions, from (b) the hydrogen and the chloride ions.

9. A method comprising:
placing a housing in a vicinity of a nerve of a subject such that an interior of a chamber defined by the housing is in fluid communication with the nerve, wherein at least one wall of the chamber includes a membrane that separates the interior of the chamber from a region outside the chamber;
driving a current between a first site within the chamber and a second site in the region outside the chamber, the second site being in a vicinity of the membrane; and
configuring the current to increase a pH in the interior of the chamber sufficiently to inhibit action potentials traveling in the nerve past the chamber.

10. The method according to claim 9,
wherein driving the current comprises driving a first current between the first and second sites,
further comprising applying a second current to the nerve that generates action potentials traveling in first and second directions in the nerve,
wherein configuring the current comprises configuring the first current to increase the pH sufficiently to block propagation past the chamber of at least a portion of the generated action potentials traveling in the second direction, and
wherein driving the first current comprises driving the first current not in coordination with the driving of the second current.

11. The method according to claim 9, wherein driving the current comprises driving the current substantially continuously for a period of time that is greater than one minute.

12. The method according to claim 11, wherein driving the current comprises driving the current substantially continuously for a period of time that is greater than one hour.

13. The method according to claim 9, wherein configuring the current comprises generating an increased level of sodium and hydroxide ions inside the chamber.

14. The method according to claim 13, wherein configuring the current comprises inhibiting action potentials traveling in the nerve past the chamber by facilitating diffusion of the sodium and the hydroxide ions into the nerve.

15. The method according to claim 13, wherein configuring the current comprises generating an increased level of hydrogen and chloride ions in the region outside the chamber.

16. The method according to claim 15, wherein placing the housing in the vicinity of the nerve comprises separating, using the membrane, (a) the sodium and the hydroxide ions, from (b) the hydrogen and the chloride ions.

* * * * *